US00PP34907P2

(12) United States Plant Patent
Bernuetz

(10) Patent No.: US PP34,907 P2
(45) Date of Patent: Jan. 10, 2023

(54) ***EUPHORBIA* PLANT NAMED 'BONPRI 1516'**

(50) Latin Name: ***Euphorbia pulcherrima* Willd. ex Klotzsch X *Euphorbia cornastra***
Varietal Denomination: BONPRI 1516

(71) Applicant: Andrew Bernuetz, Mulgoa (AU)

(72) Inventor: Andrew Bernuetz, Mulgoa (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 8 days.

(21) Appl. No.: 17/739,043

(22) Filed: May 6, 2022

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 6/385; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Euphorbia* plant named 'BONPRI 1516', characterized by its relatively compact, upright and mounded plant habit; vigorous growth habit; freely branching habit; inflorescences with deep red-colored flower bracts; and good post-production longevity.

1 Drawing Sheet

Figure 1:
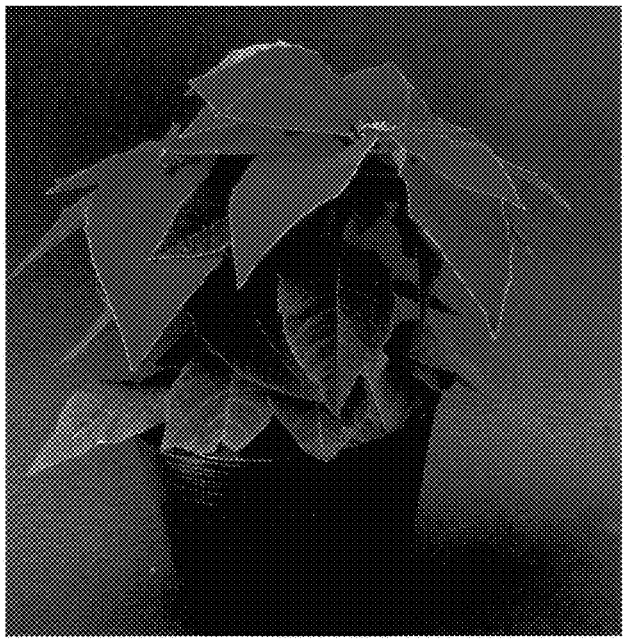

Botanical designation: *Euphorbia pulcherrima* Willd. ex Klotzsch X *Euphorbia cornastra.*

Cultivar denomination: 'BONPRI 1516'.

STATEMENT REGARDING PRIOR DISCLOSURES BY THE INVENTOR/APPLICANT & ASSIGNEE

The Inventor/Applicant and Assignee, Bonza Botanicals Pty., Ltd. of Yellow Rock, New South Wales, Australia, assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'BONPRI 1516'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch X *Euphorbia cornastra* identified as code number 917.2, not patented. The new *Euphorbia* plant was discovered and selected by the Inventor as a single flowering plant from within a population of plants of the mutation parent selection in a controlled greenhouse environment in Yellow Rock, New South Wales, Australia in January, 2015.

Asexual reproduction of the new *Euphorbia* plant by terminal vegetative cuttings in a controlled greenhouse environment in Yellow Rock, New South Wales, Australia since January, 2015 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BONPRI 1516'. These characteristics in combination distinguish 'BONPRI 1516' as a new and distinct *Euphorbia* plant:

1. Relatively compact, upright and mounded plant habit.
2. Vigorous growth habit.
3. Freely branching habit.
4. Inflorescences with deep red-colored flower bracts.
5. Good post-production longevity.

Plants of the new *Euphorbia* differ primarily from plants of the mutation parent selection in flower bract color as flower bracts of plants of the new *Euphorbia* are deep red in color whereas flower bracts of plants of the mutation parent selection are pinkish red in color.

Plants of the new *Euphorbia* can be compared to plants of the *Euphorbia pulcherrima* Willd. ex Klotzsch X *Euphorbia cornastra* 'BONPRI 9172', disclosed in U.S. Plant Pat. No. 27,720. In side-by-side comparisons, plants of the new *Euphorbia* differ primarily from plants of 'BONPRI 9172' in the following characteristics:

1. Plants of the new *Euphorbia* are more compact than plants of 'BONPRI 9172'.

2. Plants of the new *Euphorbia* have shorter lateral stems and internodes than plants of 'BONPRI 9172'.
3. Plants of the new *Euphorbia* have longer leaves than plants of 'BONPRI 9172'.
4. Plants of the new *Euphorbia* have smaller inflorescences with fewer and smaller flower bracts than plants of 'BONPRI 9172'.
5. Plants of the new *Euphorbia* and 'BONPRI 9172' differ in flower bract color as flower bracts of plants of the new *Euphorbia* are darker red in color than flower bracts of plants of 'BONPRI 9172'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the photographic sheet (FIG. 1) is a side perspective view of a typical flowering plant of 'BONPRI 1516' grown in a container.

Figure 2:
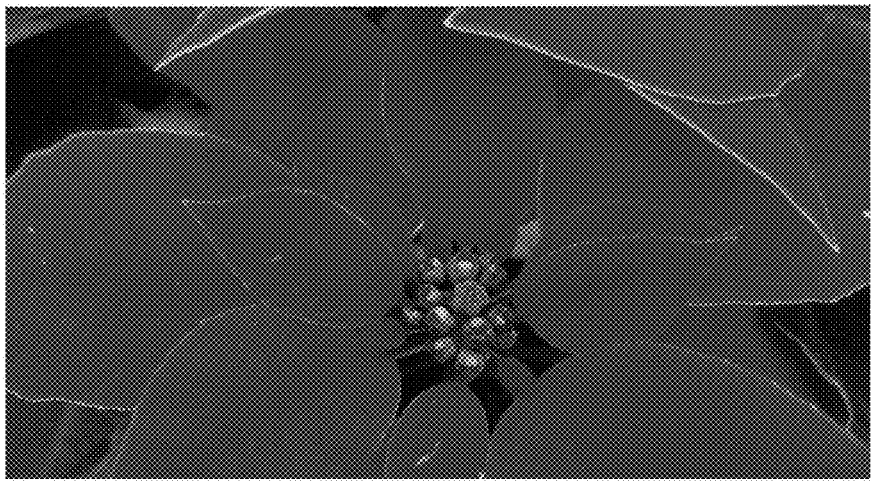

The photograph at the bottom of the photographic sheet (FIG. 2) is a close-up view of a typical inflorescence of 'BONPRI 1516'.

DETAILED BOTANICAL DESCRIPTION

Plants used in the aforementioned photographs and described herewith in detail were grown during the autumn and early winter in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'BONPRI 1516'.

Parentage: Naturally-occurring whole plant mutation of a proprietary selection of *Euphorbia pulcherrima* Willd. ex Klotzsch X *Euphorbia cornastra* identified as code number 917.2, not patented.

Propagation:

*Type*.—Terminal vegetative cuttings.

*Time to initiate roots, summer*.—About seven days at temperatures about 20° C. to 25° C.

*Time to initiate roots, winter*.—About eight days at temperatures about 20° C. to 25° C.

*Time to produce a rooted young plant, summer*.—About three weeks at temperatures about 20° C. to 25° C.

*Time to produce a rooted young plant, winter*.—About four weeks at temperatures about 20° C. to 25° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Relatively compact, upright and mounded plant habit; inverted triangle; inflorescences positioned above the foliar plane; vigorous growth habit.

*Plant height*.—About 17.2 cm.

*Plant diameter or spread*.—About 24.6 cm.

*Lateral branch description*.—Branching habit: Freely branching habit, about four lateral branches develop per plant. Length: About 11.2 cm. Diameter: About 3.4 mm. Internode length: About 2.3 cm. Aspect: Mostly upright to somewhat outward. Strength: Moderately strong. Texture and luster: Sparsely pubescent; glossy. Color: Close to 146A.

*Leaf description*.—Arrangement: Alternate, simple. Length: About 7.1 cm. Width: About 4.1 cm. Shape: Ovate. Apex: Acute. Base: Rounded. Margin: Mostly entire, occasionally with few shallow lobes. Venation pattern: Pinnate, reticulate. Texture and luster, upper and lower surfaces: Sparsely pubescent; matte. Color: Developing leaves, upper surface: Close to NN137A. Developing leaves, lower surface: Close to 147B. Fully developed leaves, upper surface: Close to NN137A and 139A; venation, close to 144D and 179D. Fully developed leaves, lower surface: Close to NN137C; venation, close to 145B. Petioles: Length: About 2.3 cm. Diameter: About 1.5 mm. Texture, upper and lower surfaces: Sparsely pubescent. Color, upper surface: Close to 183B. Color, lower surface: Close to 145B; slightly tinged with close to 183B.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about four inflorescences develop per plant.

*Inflorescence diameter*.—About 11.6 cm.

*Inflorescence height*.—About 1.7 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 50 days under natural season or photoinductive conditions in Japan.

*Post-production longevity*.—Good post-production longevity; plants of the new *Euphorbia* maintain good substance and bract color for about eight weeks.

*Flower bracts*.—Quantity per inflorescence: About nine. Length: About 4.9 cm. Width: About 2.8 cm. Shape: Ovate. Apex: Acute. Base: Obtuse. Margin: Entire with occasional irregular shallow serrations. Texture, upper surface: Smooth, glabrous. Texture, lower surface: Sparsely pubescent. Aspect: Mostly horizontal. Venation pattern: Pinnate, reticulate. Color: Transitional bracts, upper surface: Random sectors, close to 53B, 200A and 200B. Transitional bracts, lower surface: Random sectors, close to 138B, 55B and 8D. Developing bracts, upper surface: Close to 53A. Developing bracts, lower surface: Close to 53C. Fully expanded bracts, upper surface: Close to 53B; venation, close to 183B; color does not change with subsequent development. Fully expanded bracts, lower surface: Close to 53C; venation, close to 145C; color does not change with subsequent development. Flower bract petioles: Length: About 8.4 mm. Diameter: About 1.5 mm. Texture, upper and lower surfaces: Smooth, glabrous. Color, upper surface: Close to 53B and proximally, close to 180C. Color, lower surface: Close to 145A.

*Cyathia*.—Quantity per corymb: About twelve. Diameter of cyathia cluster: About 1.8 cm. Height, individual cyathium: About 5.6 mm. Diameter, individual cyathium: About 5.3 mm. Shape, individual cyathium: Globose. Color: Distally, close to 60B; mid-section and proximally, close to 144A. Nectaries: Quantity per cyathium: One. Size: About 1.9 mm by 2.9 mm. Texture: Smooth, glabrous. Color: Close to 13C and 42D.

*Peduncles*.—Length: About 2.6 mm. Diameter: About 1.5 mm. Texture, upper and lower surfaces: Smooth, glabrous. Aspect: Mostly upright. Color, upper and lower surfaces: Close to 145A.

*Reproductive organs*.—To date, stamen and pistil development have not been observed on plants of the new *Euphorbia*.

*Seeds and fruits*.—To date, seed and fruit development have not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'BONPRI 1516' as illustrated and described.

* * * * *